(12) United States Patent
Jones et al.

(10) Patent No.: US 6,286,361 B1
(45) Date of Patent: *Sep. 11, 2001

(54) METHOD AND APPARATUS FOR REMOTELY DETECTING PRESSURE, FORCE, TEMPERATURE, DENSITY, VIBRATION, VISCOSITY AND SPEED OF SOUND IN A FLUID

(75) Inventors: Alan R Jones; John R Webster; Ian D Brown, all of Derby; Duncan Pollard, Hull; Rodney D Greenough, Doncaster, all of (GB)

(73) Assignee: Rolls-Royce plc, London (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/002,866

(22) Filed: Jan. 5, 1998

(51) Int. Cl.[7] .............................. G01N 9/10; G01N 11/16
(52) U.S. Cl. .................... 73/24.05; 73/24.06; 73/30.02; 73/30.04; 73/31.05; 73/32 A; 73/54.26; 73/54.38; 73/54.41; 73/61.79; 73/64.53
(58) Field of Search ................. 73/660, 668, 861.08, 73/861.13, 861.18, 579, 643, 24.01, 31.05, 54.01–54.02, 54.23–54.27, 54.38, 54.41, 61.49, 52, 61.75, 61.79, 64.53, 597–598, 602, 644, 64.45–64.46, 23.28–23.29, 24.05, 24.06, 30.04, 30.02, 32 A (56) References Cited

U.S. PATENT DOCUMENTS

| | | | | |
|---|---|---|---|---|
| 2,550,052 | * | 4/1951 | Fay | 73/59 |
| 3,474,663 | * | 10/1969 | Whitmer et al. | 73/59 |
| 3,712,117 | * | 1/1973 | Fitzgerald et al. | 73/59 |
| 3,796,088 | * | 3/1974 | Gustafsson et al. | 73/59 |
| 3,805,592 | * | 4/1974 | Miller et al. | 73/32 R |
| 4,020,678 | * | 5/1977 | Laue | 73/579 |
| 4,177,434 | * | 12/1979 | ida | 73/59 |
| 4,193,291 | * | 3/1980 | Lynnworth | 73/32 A |
| 4,350,043 | * | 9/1982 | Jones | 73/579 |
| 4,389,891 | * | 6/1983 | Fournier | 73/579 |
| 4,493,215 | * | 1/1985 | Gast et al. | 73/861.18 |
| 4,783,987 | * | 11/1988 | Hager et al. | 73/32 A |

(List continued on next page.)

FOREIGN PATENT DOCUMENTS

| | | |
|---|---|---|
| 2039369 | 12/1979 | (GB) . |
| 2099998 | 5/1982 | (GB) . |
| 2143325 | 2/1985 | (GB) . |
| 57053636A | 3/1982 | (JP) . |
| 2021233 | 1/1990 | (JP) . |
| 4148825 | 5/1992 | (JP) . |

Primary Examiner—Hezron Williams
Assistant Examiner—Rose M. Miller
(74) Attorney, Agent, or Firm—W. Warren Taltavull; Manelli Denison & Selter PLLC (57) ABSTRACT

An apparatus for detecting pressure in a hollow fan blade of a turbofan gas turbine engine comprises a magnetostriction transducer arranged in a sub chamber of the fan blade which is interconnected to a main chamber. A magnetic coil is arranged in the fan casing of the turbofan remote from the fan blade, and an alternating current is supplied from a supply to the magnetic coil to produce an alternating magnetic field. The alternating magnetic field causes the magnetostriction transducer to generate vibrations in the fan blade and the magnetostriction transducer. A magnetic search coil detects changes in the magnetic field, which corresponds to the vibrations, and a processor analyses the vibrations to determine if there has been a change in the resonant frequency of the vibrations which is indicative of a change in the pressure in the fan blade. The processor supplies a signal to a display or to an alarm. The change in the pressure is indicative that the fan blade is cracked and needs replacing.

37 Claims, 7 Drawing Sheets

U.S. PATENT DOCUMENTS

| | | | | |
|---|---|---|---|---|
| 4,924,706 | * | 5/1990 | Moore | 73/579 |
| 5,152,172 | * | 10/1992 | Leon et al. | 73/579 |
| 5,303,595 | | 4/1994 | Shoji . | |
| 5,394,739 | * | 3/1995 | Garvey, III et al. | 73/54.23 |
| 5,627,380 | * | 5/1997 | Crowne | 73/313 |
| 5,686,661 | * | 11/1997 | Singh et al. | 73/655 |
| 5,798,454 | * | 8/1998 | Nakazeki et al. | 73/54.28 |
| 5,821,430 | * | 10/1998 | Kwun et al. | 73/581 |
| 5,844,140 | * | 12/1998 | Seale | 73/633 |

* cited by examiner

METHOD AND APPARATUS FOR REMOTELY DETECTING PRESSURE, FORCE, TEMPERATURE, DENSITY, VIBRATION, VISCOSITY AND SPEED OF SOUND IN A FLUID

FIELD OF THE INVENTION

The present invention relates to the detection of pressure or temperature, and in particular to the remote detection of pressure, force, temperature, density, vibration, viscosity and speed of sound in a fluid in hollow articles.

BACKGROUND OF THE INVENTION

The failure of mechanical articles, or components, by fatigue cracking can occur if the article, or components, are exposed to cyclic loading or vibrations. The failure of a fan blade of a turbofan gas turbine engine by fatigue cracking is unacceptable and cracks must be detected before they reach a size at which they could cause the fan blade failure. The fan blades of some turbofan gas turbine engines are hollow, and the cracks are most likely to form through the walls defining the hollow chamber in the fan blades. These hollow fan blades are evacuated during the manufacturing process.

A known method of detecting cracks in hollow fan blades is to place a piezoelectric transducer on the surface of the hollow fan blade such that it is acoustically coupled to the hollow fan blade. The piezoelectric transducer is electrically excited to generate ultrasound at a particular frequency, for example 150 kHz, in the hollow fan blade. The piezoelectric transducer is then used to detect the ultrasound in the hollow fan blade and an analyser is used to monitor the decay rate of the amplitude of the ultrasound at the particular frequency. It has been found that the decay rate of the amplitude of the ultrasound at the particular frequency is proportional to the pressure in the hollow fan blade. Thus if there is a crack in the hollow fan blade the pressure is greater in the hollow fan blade than for an uncracked fan blade and therefore the decay rate for the cracked hollow fan blade has a higher decay rate than for an uncracked hollow fan blade.

The inspection of a full set of hollow fan blades on a turbofan gas turbine engine is extremely time consuming. The inspection of the hollow fan blades requires an inspector to couple the piezoelectric transducer to, and to test, each hollow fan blade in turn.

The prior art method and apparatus for detecting these pressure within the hollow fan blade is not automatic, is time consuming and requires contact between the detection apparatus and the hollow fan blade.

SUMMARY OF THE INVENTION

The present invention seeks to provide a method and apparatus for detecting the pressure, force, temperature, density, vibration, viscosity and speed of sound in a fluid in an article which overcomes the above mentioned problems.

Accordingly the present invention provides a method of remotely detecting pressure, force, temperature, density, vibration, viscosity or speed of sound in a fluid, the method comprising:

providing at least one magnetostriction transducer, providing means to produce a varying magnetic field in spaced apart relationship with the magnetostriction transducer, producing a varying magnetic field such that the varying magnetic field acts upon the at least one magnetostriction transducer to generate vibrations in the at least one magnetostriction transducer, providing means to detect the vibrations in spaced apart relationship with the magnetostriction transducer, detecting the vibrations generated in the at least one magnetostriction transducer by the varying magnetic field, and analysing the detected vibrations to determine the pressure, force, temperature, density, vibration, viscosity or speed of sound in a fluid.

The magnetostriction transducer may be located in an article. The article may be a hollow article.

The analysing of the detected vibrations may be by analysing the amplitude and/or the frequency and/or these damping and/or the phase.

The analysing of the damping may be by detecting the decay rate of the amplitude of the vibrations in the at least one magnetostriction transducer or the article at a particular frequency.

The analysing of the frequency may be by detecting changes in the resonant frequency of the vibrations in the at least one magnetostriction transducer or the article.

The analysing of the frequency may be by detecting changes in the amplitude of the vibrations in the at least one magnetostriction transducer or the article at or around the resonant frequency.

The analysing of the frequency may be by detecting changes in the magnetic flux.

There may be two magnetostriction transducers in the hollow article, a first one of the magnetostriction transducers is in communication with the hollow interior of the hollow article and the second one of the magnetostriction transducers is not in communication with the hollow interior of the hollow article, the magnetostriction transducers having different resonant frequencies.

The vibrations may be ultrasounds.

The analysing may comprise displaying the pressure, force, temperature, density, vibration, viscosity or speed of sound in a fluid. The analysing may comprise produce a warning that the pressure, force, temperature, density, vibration, viscosity or speed of sound in a fluid is at a predetermined level.

The present invention also provides an apparatus for remotely detecting pressure, force, temperature, density, vibration, viscosity or speed of sound in a fluid comprising, at least one magnetostriction transducer, means to produce a varying magnetic field arranged in spaced apart relationship with the magnetostriction transducer such that a varying magnetic field acts upon the at least one magnetostriction transducer to generate vibrations in the at least one magnetostriction transducer, means to detect the vibrations generated in the at least one magnetostriction transducer, the means to detect the vibrations is arranged in spaced apart relationship with the magnetostriction transducer, and analysing means to analyse the detected vibrations to determine the pressure, force, temperature, density, vibration, viscosity or speed of sound in a fluid.

The magnetostriction transducer may be located in an article. The article may be a hollow article.

The means to analyse the detected vibrations may be means to analyse the amplitude and/or the frequency and/or the damping and/or the phase.

The means to analyse the damping may be means to detect the decay rate of the amplitude of the vibrations in the at least one magnetostriction transducer or the article at a particular frequency.

The means to analyse the frequency may be means to detect changes in the resonant frequency of the vibrations in the at least one magnetostriction transducer or the article.

The means to analyse the frequency may be means to detect changes in the amplitude of the vibrations in the at least one magnetostriction transducer or the article at or around the resonant frequency.

There may be two magnetostriction transducers in the hollow article, a first one of the magnetostriction transducers is in communication with the hollow interior of the hollow article and the second one of the magnetostrictior transducers is not in communication with the hollow interior of the hollow article, the magnetostriction transducers having different resonant frequencies.

The at least one magnetostriction transducer may comprise a magnetostrictive member and a damping member secured to the magnetostrictive member, the damping member having a large surface area.

The at least one magnetostriction transducer may comprise a magnetostrictive plate and a damping plate secured to one face of the magnetostrictive plate.

The at least one magnetostriction transducer may comprise a magnetostrictive member arranged in a sealed chamber, the sealed chamber is evacuated.

The sealed chamber may be defined by at least one flexible wall, the flexible wall may be arranged permanently in contact with the magnetostrictive member or may be arranged to move into and out of contact with the magnetostrictive member. The magnetostriction transducer may comprise a rigid cylindrical wall having a rigid end wall and a flexible end wall defining the sealed chamber and a magnetostrictive member extending between and contacting the rigid end wall and the flexible end wall. There may be mechanical means to prestress the magnetostrictive member.

The rigid walls and the flexible wall are low magnetic permeability materials.

The rigid walls may comprise stainless steel and the flexible wall may comprise brass.

The magnetostriction transducer may have magnetic means to magnetically bias the magnetostrictive member.

The means to detect the vibrations may comprise an air coupled acoustic transducer, or a laser interferometer to directly detect the vibrations of the magnetostriction transducer or the article.

The means to detect the vibrations may comprise a coil of wire to detect changes in the generated magnetic field, which corresponds to the vibrations of the magnetostriction transducer.

The means to produce an alternating magnetic field may comprise a coil of wire.

The means to detect the vibrations may comprise the coil of wire used to produce the alternating magnetic field, the coil of wire detects changes in the generated magnetic field, which corresponds to the vibrations of the magnetostriction transducer.

The hollow article may be a turbofan gas turbine engine fan blade. The means to detect the vibrations may be arranged on a fan casing enclosing the fan blade.

The present invention also provides a magnetostriction transducer comprising a magnetostrictive member arranged in a sealed chamber, the sealed chamber is evacuated, the sealed chamber is defined by at least one flexible wall, the flexible wall is arranged permanently in contact with the magnetostrictive member or is arranged to move into and out of contact with the magnetostrictive member.

The magnetostriction transducer may comprise a rigid cylindrical wall having a rigid end wall and a flexible end wall defining the sealed chamber and a magnetostrictive member extending between and contacting the rigid end wall and the flexible end wall.

The magnetostrictive member may comprise an alloy of terbium, dysprosium and iron.

BRIEF DESCRIPTION OF THE DRAWINGS

The present invention will be more fully described by way of example with reference to the accompanying drawings, in which.

DETAILED DESCRIPTION

Figure 1:
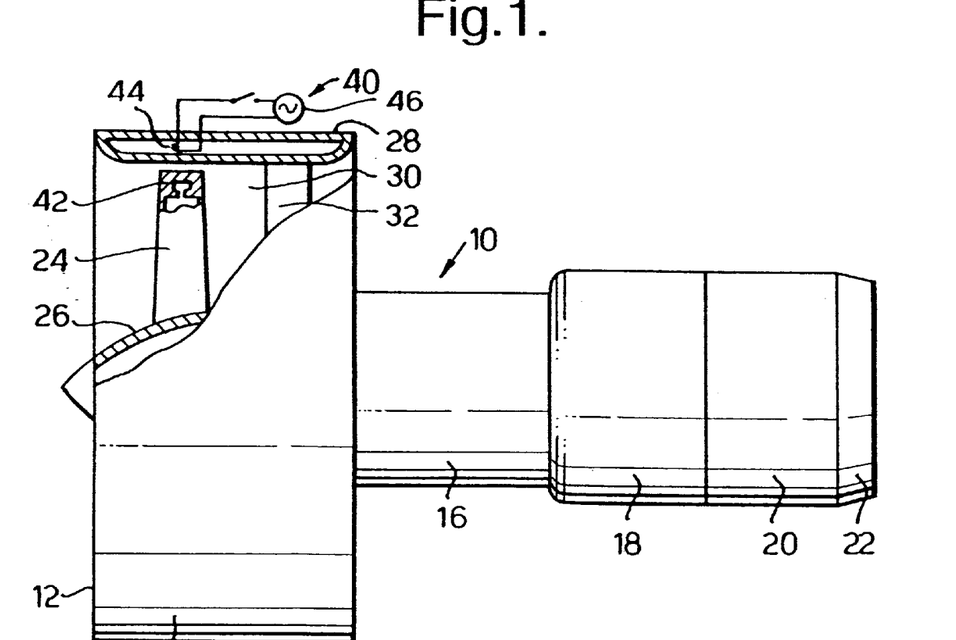
FIG. 1 is a partially cut away view of a turbofan gas turbine engine having an apparatus for remotely detecting pressure or temperature in a hollow article according to the present invention.

A turbofan gas turbine engine 10 is shown in FIG. 1 and comprises in axial flow series an inlet 12, a fan section 14, a compressor section 16, a combustion section 18, a turbine section 20 and an exhaust 22. The turbine section 20 is arranged to drive the fan section 14 and compressor section 16 via one or more shafts. The turbofan gas turbine engine 10 operates conventionally and its operation will not be discussed further.

The fan section 14 comprises a plurality of fan blades 24 secured to and extending radially from a fan rotor 26. The fan blades 24 are enclosed by a fan casing 28, which defines a fan duct 30, and the fan casing 28 is secured to the compressor casing by a plurality of radially extending fan outlet guide vanes 32.

It is known to make the fan blades 24 hollow so as to reduce the weight of the fan blades. It is also known that these fan blades 24 are manufactured by diffusion bonding, or diffusion brazing, a honeycomb core between two outer metallic sheets or by diffusion bonding and superplastically forming a metallic core sheet between two metallic outer sheets to define a hollow interior 34. It is also known to simply use two outer sheets to define a hollow interior 34. As a result of the manufacturing process the hollow interior 34 of the fan blade 24 is at vacuum pressure.

As discussed previously there is a known method of detecting cracks in hollow fan blades in which a piezoelectric transducer is placed on the surface of the hollow fan blade such that it is acoustically coupled to the hollow fan blade. The piezoelectric transducer is electrically excited to generate ultrasound at a particular frequency, for example 150 kHz, in the hollow fan blade. The piezoelectric transducer is then used to detect the ultrasound in the hollow fan blade and an analyser is used to monitor the decay rate of the amplitude of the ultrasound at the particular frequency. It has been found that the decay rate of the amplitude of the ultrasound at the particular frequency is proportional to the pressure in the hollow fan blade. If there is a crack in the hollow fan blade, air enters the hollow fan blade and the pressure in the hollow fan blade rises to atmospheric pressure. Thus if there is a crack in the hollow fan blade the pressure is greater in the hollow fan blade than for an uncracked fan blade and therefore the decay rate for the cracked hollow fan blade has a higher decay rate than for an uncracked hollow fan blade.

The prior art method and apparatus for detecting the pressure within the hollow fan blade is not automatic, is time consuming and requires contact between the detection apparatus and the hollow fan blade.

Figure 2:
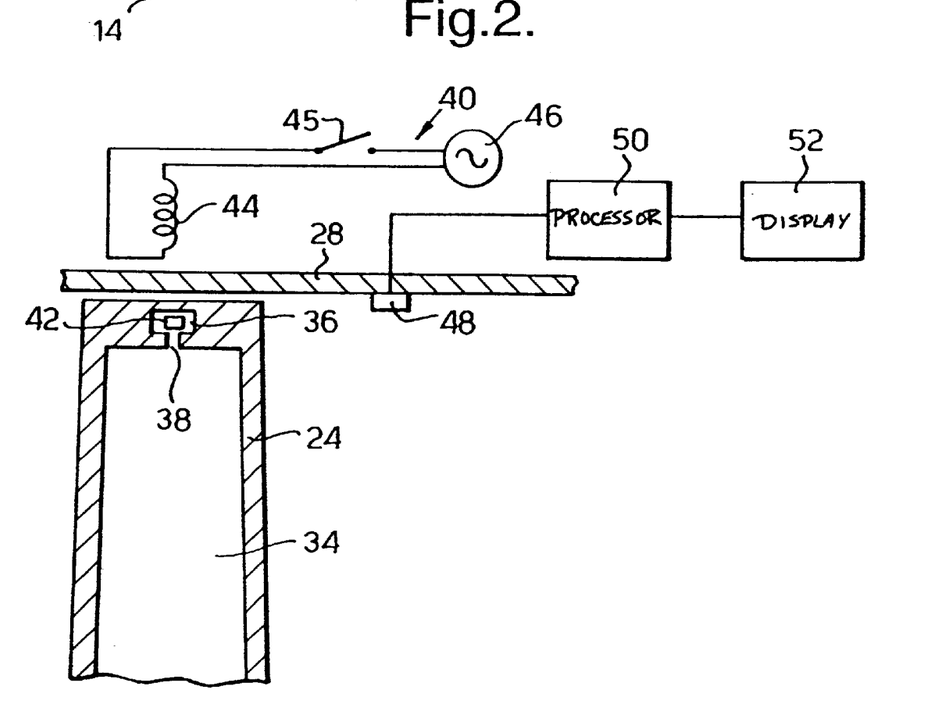
FIG. 2 is an enlarged view of one embodiment of an apparatus for remotely detecting pressure or temperature in a hollow article according to the present invention.

The invention provides an apparatus 40 for remotely detecting pressure in a hollow article, as shown in FIGS. 1 and 2, for example a turbofan gas turbine engine fan blade 14. The apparatus 40 comprises a magnetostriction transducer 42 placed within a small sub-chamber 36 at the tip of the fan blade 24 adjacent to, but spaced from, the fan casing 28. The sub-chamber 36 is interconnected to the hollow interior 34 by a passage 38.

A magnetic coil 44 is positioned remotely from the hollow fan blade 24 within the fan casing 28, and the magnetic coil 44 is connected to a source of alternating current 46 via a switch 45, such that when the switch 45 is closed the alternating current supplied to the magnetic coil 44 produces an alternating magnetic field.

An air coupled transducer 48, a microphone, is arranged on the fan casing 28 to detect vibrations, particularly ultrasounds, emitted from the hollow fan blade 24, and the air coupled transducer 48 is connected to a processor 50 which analyses the detected ultrasound to determine if the pressure in the hollow fan blade 24 has changed. The processor 50 is connected to a display 52 to indicate the actual pressure in the hollow fan blade, and/or to a warning device to indicate that the hollow fan blade 24 is cracked.

The alternating magnetic field produced by the magnetic coil 44 is at an ultrasonic frequency, although lower frequencies may be used, and passes through the wall of the hollow fan blade 24 to the hollow interior 34 of the fan blade 24. The alternating magnetic field acts upon the magnetostriction transducer 42 and causes mechanical movement of the magnetostriction transducer 42 which in turn generates ultrasound.

The air coupled transducer 48 is tuned to the resonant frequency of the magnetostriction transducer 42, or to the frequency at which the magnetostriction transducer 42 is excited, and the processor 50 analyses the ultrasound for a short period of time to determine if the decay rate of the amplitude of the ultrasound at the particular frequency has changed, for example increased. The processor 50 is arranged to send a signal to the display 52 to indicate the pressure, and/or the processor 50 is arranged to send a signal to an alarm to indicate that the fan blade 24 is cracked or both. The processor 50 may compare the detected decay rate of the amplitude of the ultrasound at the particular frequency with a range of acceptable decay rates, and if the detected decay rate is outside the range of acceptable decay rates sends an appropriate signal to the display or alarm.

The air coupled transducer, may be replaced by a laser interferometer arranged on the fan casing, or other static structure of the gas turbine engine, and the laser interferometer is arranged to view a suitable region of the fan blade or by a magnetoelastic glass transducer coupled to the fan blade to detect vibrations and a hall effect transducer or coil in the fan casing to detect magnetic fields produced by the magnetoelastic transducer.

Figure 3:
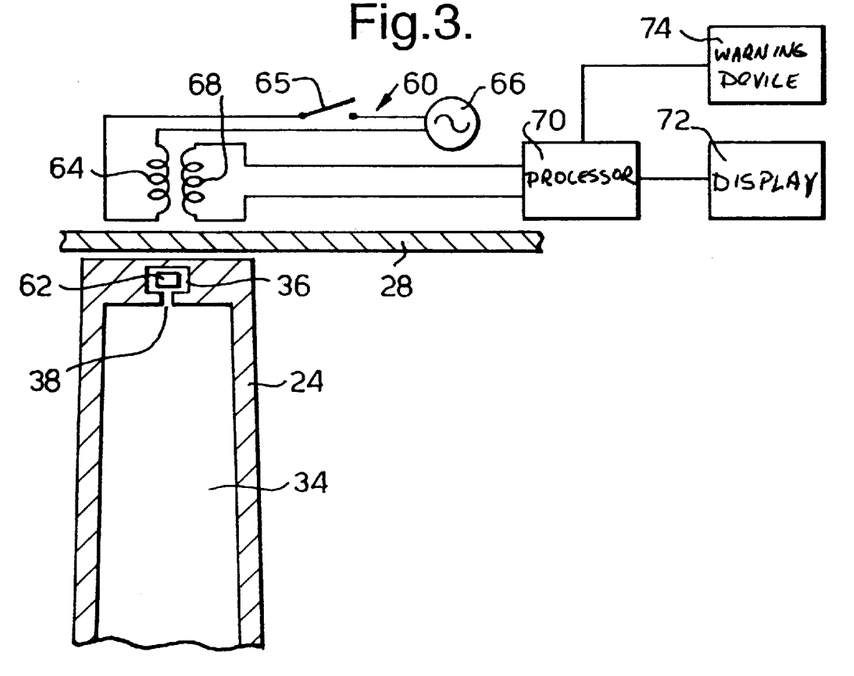
FIG. 3 is an enlarged view of an alternative embodiment of an apparatus for remotely detecting pressure or temperature in a hollow article according to the present invention.

The invention also provides an apparatus 60 for remotely detecting pressure in a hollow article, as shown in FIGS. 1 and 3, for example a turbofan gas turbine engine fan blade 24. The apparatus 60 comprises a magnetostriction transducer 62 placed within a small sub-chamber 36 at the tip of the fan blade 24 adjacent to, but spaced from, the fan casing 28. The sub-chamber 36 is interconnected to the hollow interior 34 by a passage 38.

A magnetic coil 64 is positioned remotely from the hollow fan blade 24 within the fan casing 28, and the magnetic coil 64 is connected to a source of alternating current 66 via a switch 65, such that when the switch 65 is closed the alternating current supplied to the magnetic coil 64 produces an alternating magnetic field.

A magnetic search coil 68 is arranged on the fan casing 28 to indirectly detect the ultrasound generated in the hollow fan blade 24 and/or the magnetostriction transducer 62. The magnetic search coil 68 is connected to a processor 70 which analyses the detected ultrasound to determine if the pressure in the hollow fan blade 24 has changed. The processor 70 is connected to a display 72 to indicate the actual pressure in the hollow fan blade, and/or to a warning device 74 to indicate that the hollow fan blade 24 is cracked.

The alternating magnetic field produced by the magnetic coil 64 is at an ultrasonic frequency and passes through the wall of the hollow fan blade 24 to the hollow interior 34 of the fan blade 24. The alternating magnetic field acts upon the magnetostriction transducer 62 and causes mechanical movement of the magnetostriction transducer 62 which in turn generates ultrasound in the fan blade 24 and the magnetostriction transducer 62.

The frequency of the applied magnetic field produced by the magnetic coil 64 is swept over a narrow frequency range around the resonant frequency of the magnetostriction transducer 62. The magnetostriction transducer 62 removes energy from the magnetic field generated by the magnetic coil 64 in order to cause the magnetostriction transducer to vibrate. The magnetostriction transducer 62 therefore reduces the strength of the magnetic field at the resonant frequency of the magnetostriction transducer 62. The magnetic search coil 68 detects the changes, the reduction, in the magnetic flux at the resonant frequency of the magnetostriction transducer 62 produced by the magnetostriction transducer 62 as a result of the vibrations being generated in the fan blade 24 and the magnetostriction transducer 62. The processor 70 analyses the magnetic field, which corresponds to the vibrations in the fan blade 24, detected by the magnetic search coil 68 to determine if the ratio of the centre frequency to the bandwidth corresponding to the resonant frequency, known as the "Q factor", of the magnetostriction transducer 62 has changed. For example if the fan blade is initially evacuated there is a relatively high "Q factor" and if the fan blade is cracked to allow air to enter there is a relatively low "Q factor". The processor 70 may compare the detected "Q factor" with a range of acceptable "Q factors", and if the detected "Q factor" is outside the range of acceptable "Q factors" sends an appropriate signal to the display or alarm.

Alternatively and preferably the processor 70 analyses the magnetic field, which corresponds to the vibrations in the fan blade, detected by the magnetic search coil 68 to determine if the resonant frequency of the magnetostriction transducer 62 has changed. For example if the fan blade is initially evacuated the magnetostriction transducer has a relatively low resonant frequency and if the fan blade is cracked to allow air to enter the fan blade the magnetostriction transducer has a relatively high resonant frequency. The processor 70 may compare the detected resonant frequency with a range of acceptable resonant frequencies, and if the detected resonant frequency is outside the acceptable range of resonant frequencies sends an appropriate signal to the display or alarm.

The magnetostriction transducer comprises a magnetostrictive member which is preferably an alloy of terbium, dysprosium and iron, of the general formula $Tb_xDy_{1-x}Fe_{1.95}$ (where x may vary but is typically 0.3). An example of a suitable composition is sold under the trade name Terfenol D and is available from Etrema Products Inc, 2500 North Loop Drive, Ames, Iowa 50010, U.S.A. The Terfenol D is usually cast in directionally solidified or single crystal form. It is possible to use magnetostrictive members of other suitable alloys.

Figure 4:
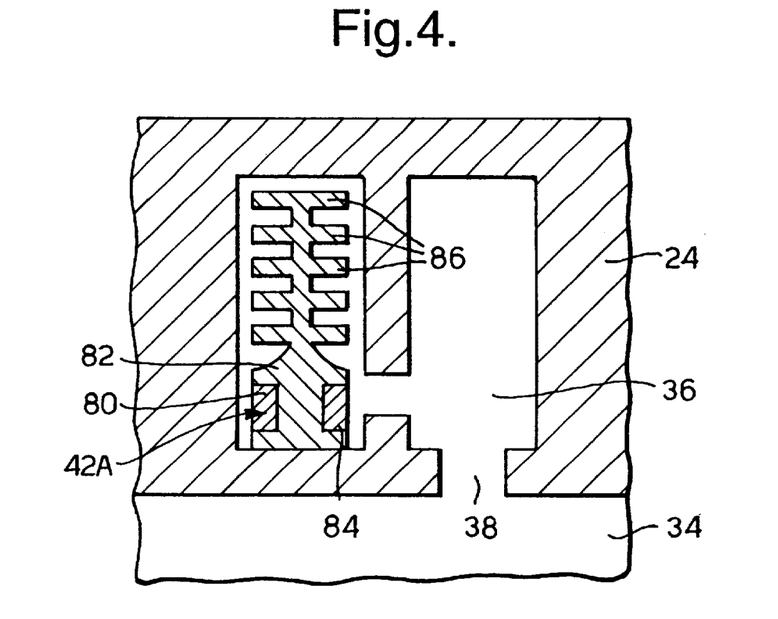
FIG. 4 is an enlarged view of a magnetostriction transducer for use in an apparatus for remotely detecting pressure or temperature in a hollow article according to the present invention.

One suitable magnetostriction transducer 42A is shown in FIG. 4 and comprises a magnetostrictive member 80 in the shape of a hollow rod which is arranged in a circular groove 84 on a damping member 82. The damping member 82 has a number of members 86 to increase the surface area to increase the damping of the movement of the magnetostrictive member 80 due to air or gas pressure.

Figure 5:
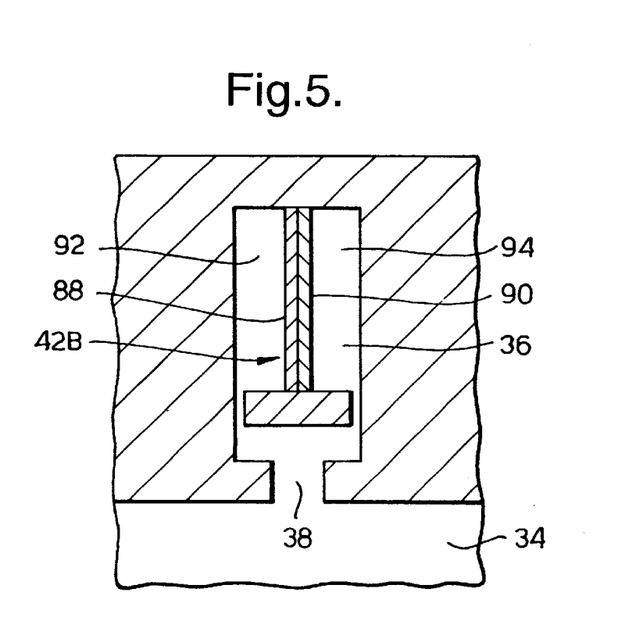
FIG. 5 is an enlarged view of an alternative magnetostriction transducer for use in an apparatus for remotely detecting pressure or temperature in a hollow article according to the present invention.

Another suitable magnetostriction transducer 42B is shown in FIG. 5 and comprises a magnetostrictive plate 88 and a damping plate 90 is secured to one face of the magnetostrictive plate 88. The edges of the magnetostrictive plate 88 and damping plate 90 are secured to the structure of the fan blade 24, or a member, to define a chamber 92 between the fan blade 24 and the magnetostriction plate 88 and to define a chamber 94 between the fan blade 24 and the damping plate 90. The hollow interior 34 of the fan blade 24 is interconnected to chambers 92 and 94.

Figure 6:
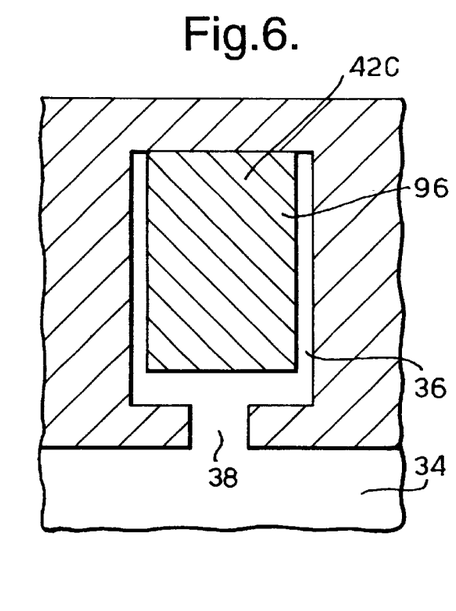
FIG. 6 is an enlarged view of an alternative magnetostriction transducer for use in an apparatus for remotely detecting pressure or temperature in a hollow article according to the present invention.

A further suitable magnetostriction transducer 42C is shown in FIG. 6 and comprises a magnetostrictive rod or hollow tube 96 secured at one end to the fan blade 24. The clearance between the unsecured surfaces of the magnetostrictive member 96 and the fan blade 24 are predetermined to maximise damping of the magnetostrictive member 96 due to air or gas pressure.

Figure 7:
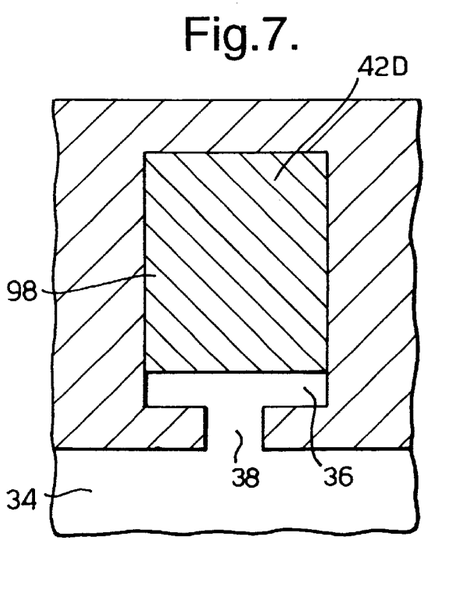
FIG. 7 is an enlarged view of an alternative magnetostriction transducer for use in an apparatus for remotely detecting pressure or temperature in a hollow article according to the present invention.

Another suitable magnetostriction transducer 42D is shown in FIG. 7 and comprises a magnetostrictive plate 98 secured along three edges to the fan blade 24 or other suitable member to form a chamber 36. The air or gas pressure in the chamber 36 determines the amount of damping of the magnetostrictive plate 98.

Figure 8:
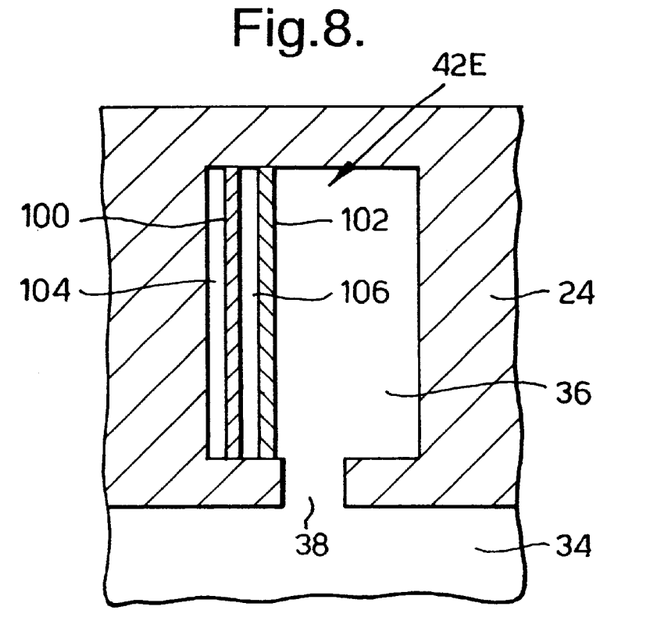
FIG. 8 is an enlarged view of an alternative magnetostriction transducer for use in an apparatus for remotely detecting pressure or temperature in a hollow article according to the present invention.

An additional magnetostriction transducer 42E is shown in FIG. 8 and comprises a magnetostrictive plate 100 secured at its edges to the fan blade 24 or other suitable member to form a chamber 104 with the fan blade 24. A flexible damping plate 102 is secured at its edges to the fan blade or other suitable member to form a chamber 106 with the magnetostrictive plate 100. The damping plate also partially defines the sub-chamber 36. The chambers 104 and 106 are evacuated. The air or gas pressure in the chamber 36 determines the amount of damping on the magnetostrictive plate 98, by causing the flexible damping plate to flex and move into contact with the magnetostrictive plate 100 when the fan blade 24 is cracked.

Figure 9:
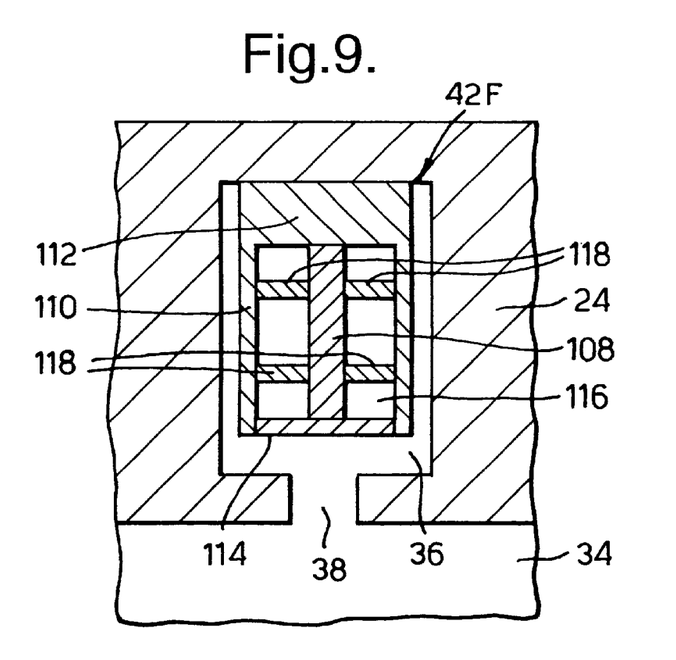
FIG. 9 is an enlarged view of an alternative magnetostriction transducer for use in an apparatus for remotely detecting pressure or temperature in a hollow article according to the present invention.

A preferred magnetostriction transducer 42F is shown in FIG. 9 and comprises an elongate magnetostrictive member 108 in the form of a rod, bar or hollow tube arranged within a rigid cylindrical wall 110 having a rigid end wall 112 and a flexible end wall 114 defining a sealed chamber 116. The magnetostrictive member 108 extends between and contacts the rigid end wall 112 and the flexible end wall 114. A plurality of elastic supports 118 are provided to support the magnetostrictive member 108. The rigid walls 110 and 112 and flexible wall 114 comprise low magnetic permeability materials.

For example the rigid walls 110 and 112 comprise non magnetic stainless steel or titanium, the flexible wall 114 comprises brass or titanium and the elastic supports 118 may comprise for example titanium springs, nylon or any other suitable elastic support. In some circumstances the rigid end wall 112 may have a large mass against which the magnetostrictive member 108 may vibrate, for example if the vibrational coupling into the hollow article is relatively low. The air or gas pressure in the chamber 36 determines the amount of axial stress on the magnetostrictive member 108.

The application of a magnetic field to the magnetostriction transducer initially makes the magnetostriction member shorter and wider for negative magnetostrictive materials or longer and thinner for positive magnetostrictive materials. In the invention as described a positive magnetostrictive material is used but negative magnetostrictive materials may be used.

The resonant frequency of the magnetostrictive member 108 varies with length, typical values are shown in Table 1, for Terfenol D with a 25 kA/m bias field and 4.5 MPa prestress and a coupling coefficient of 0.57.

TABLE 1

| Length of Terfenol D (mm) | Resonant Frequency (kHz) |
| --- | --- |
| 10 | >100 |
| 25 | 35 |
| 50 | 20 |
| 75 | 15 |
| 100 | 10 |

In tests using a Terfenol D rod having a 6 mm diameter and a length of 64 mm, and a non magnetic stainless steel cylinder having a 29 mm diameter, a length of 85 mm and a thickness of 0.2 mm with a brass flexible member. The cylinder was placed in a titanium cylinder having a 30 mm diameter, a length of 85 mm and a thickness of 1 mm to represent the fan blade. A magnetic coil of 200 turns of 38 SWG insulated copper wire was wound around the titanium cylinder. The interior of the steel cylinder was evacuated. The pressure in the titanium cylinder was varied and the effects on the resonant frequency of the Terfenol D rod was noted. As the pressure in the titanium cylinder increased gradually from vacuum to atmospheric pressure the resonant frequency of the Terfenol D rod increased linearly from 15.5 kHz to 18 kHz, i.e. a 2.5 kHz change in resonant frequency. It is believed that the same effect is applicable to shorter and longer Terfenol D rods. The magnetostriction transducer may comprise magnetic means to magnetically bias the magnetostrictive member.

The resonant frequency of the magnetostrictive member varies also with the magnetomechanical coupling factor $k_{33}$. This magnetomechanical coupling factor, in turn, varies with prestress and magnetic bias. Both the magnetic bias and the prestress must be adjusted to obtain optimum transducer performance.

The invention is also applicable to the remote detection of temperature using the same transducers as is shown in FIG. 9, except that the flexible wall is replaced by a rigid wall such that differences in thermal expansion between the magnetostrictive member and the rigid cylinder due to changes in temperature apply longitudinal stress on the magnetostrictive member. This results in changes to the resonant frequency of the magnetostrictive member and the processor and display may be arranged to indicate the temperature.

Figure 10:
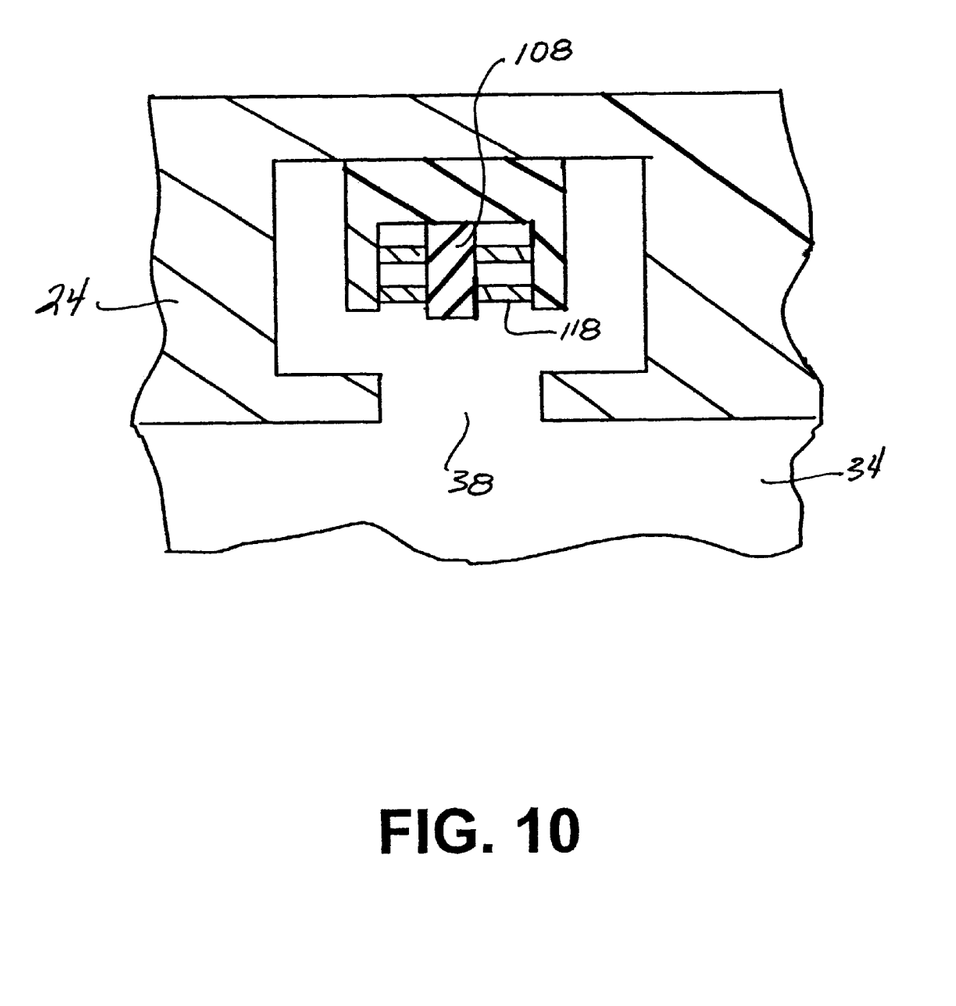
FIG. 10 is a schematic view of another embodiment of the invention for detecting force and vibration.
Figure 11:
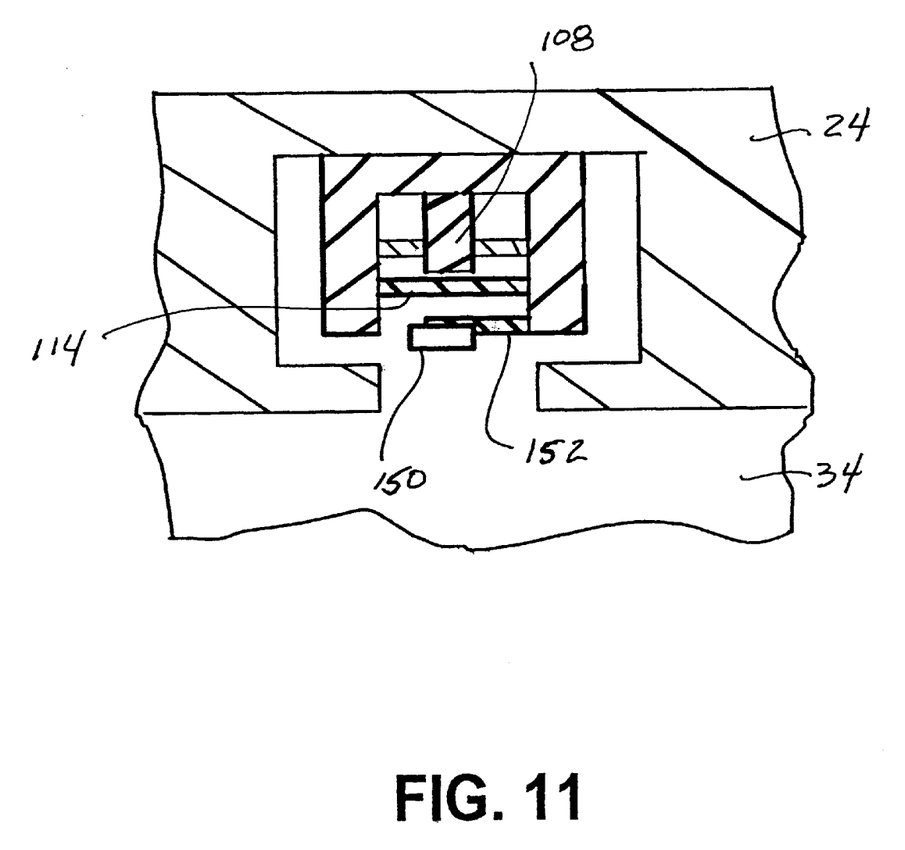
FIG. 11 is an embodiment for detecting the speed of sound in the blade.

The invention is also applicable to the remote detection of force, density, vibration, viscosity and speed of sound in a fluid. Force and vibration may be measured by directly adapting the transducer in FIG. 9 by removing the flexible wall as shown in FIG. 10 and applying the load to the now free end of the magnetostrictive member 108, as shown. Vibration is simply a dynamic force. The density of a fluid may be measured by placing the fluid in a container on the other side of the flexible wall in FIG. 9, and the change in mass/density changes the resonant frequency of the transducer. The viscosity of fluid may be measured using the transducer in FIG. 4 and measuring damping. The speed of sound in a fluid is measured by adapting the transducer in FIG. 9 by providing a sprung mass 150 as shown in FIG. 11 mounted on a flexible arm 152 to space the mass 150 in close proximity to the flexible wall 114. The fluid flows in the gap between the flexible wall and the sprung mass 150. The resonant frequency of the entire assembly is measured and this is dependent upon the speed of sound in the fluid.

A single magnetic coil may be used to produce the magnetic field to excite the magnetostriction transducer and to detect the ultrasound produced by the magnetostriction transducer.

Figure 12:
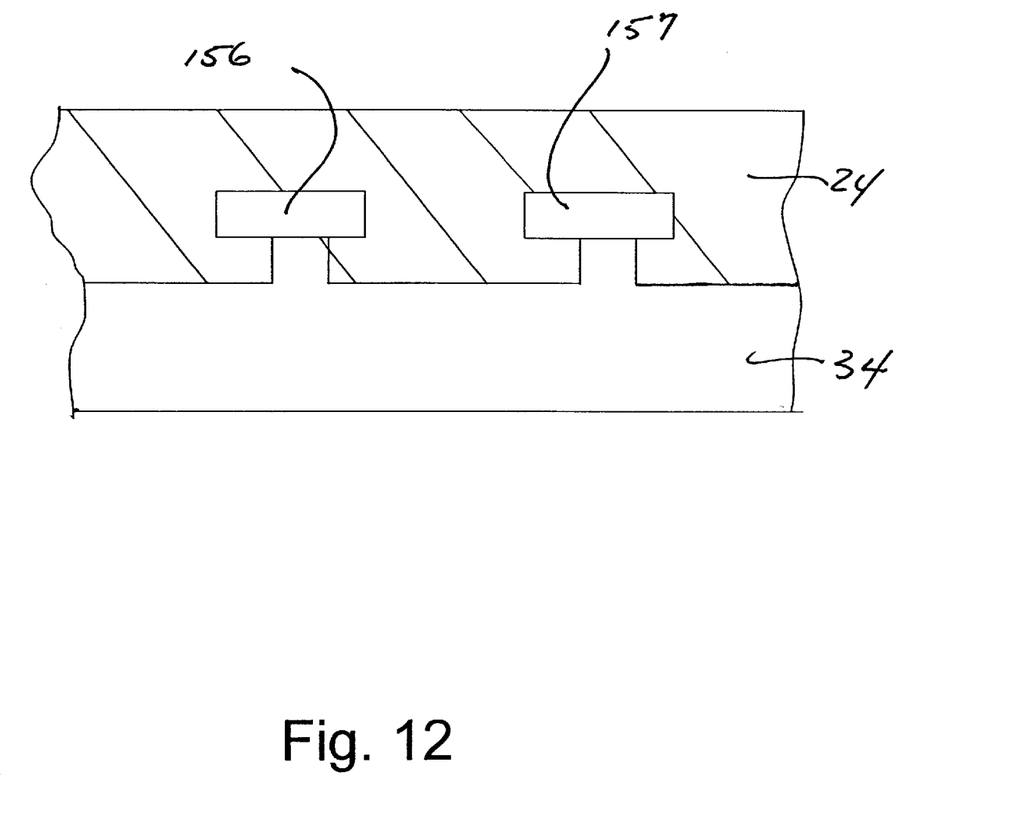
FIG. 12 is an illustration of the use of two transducers.

It may be necessary to provide two magnetostriction transducers, which are resonant at different frequencies, as shown in FIG. 12 at 156 and 157, to detect pressure changes and to ensure that only one of the magnetostriction transducers is connected to the pressure in the hollow fan blade.

The remote detection of pressure using the apparatus described enables automatic inspection of all the fan blades in an engine by providing each fan blade with a magnetostriction transducer. The inspection may be carried out during shut down of the turbofan, while turning the engine over using a starting device or during windmilling of the turbofan, the slower the speed at which the tip of the fan blade passes the magnetic coil, the longer is the time available for the magnetic coil to interrogate each magnetostriction transducer. The remote detection is non contacting, reduces the amount of time and/or the manpower required to inspect the fan blades.

The invention is applicable to remote detection of pressure in other hollow article.

We claim:
1. A method of remotely detecting at least one from the group consisting of pressure, force, temperature, density, vibration, viscosity and speed of sound in a fluid in an article, the article having an inside and an outside, the method comprising:
   providing a magnetostriction transducer located wholly in the inside of the article,
   providing means to produce a varying magnetic field in spaced apart relationship with said magnetostriction transducer, positioning the means to produce a varying magnetic field outside the article,
   producing a varying magnetic field such that the varying magnetic field acts upon said magnetostriction transducer to generate vibrations in said magnetostriction transducer,
   providing means to detect the vibrations in spaced apart relationship with said magnetostriction transducer, positioning the means to detect the vibrations outside the article,
   detecting the vibrations generated in said magnetostriction transducer by the varying magnetic field,
   and analyzing the detected vibrations to determine at least one from the group consisting of the pressure, force, temperature, density, vibration, viscosity and speed of sound in a fluid.

2. A method as claimed in claim 1 wherein the article is a hollow article.

3. A method as claimed in claim 1 wherein the analyzing of the detected vibrations is by analysing the amplitude or the frequency or the damping or the phase.

4. A method as claimed in claim 3 wherein the analyzing of the damping comprises detecting the decay rate of the amplitude of the vibrations in said magnetostriction transducer at a particular frequency.

5. A method as claimed in claim 3 wherein the analyzing of the frequency comprises detecting changes in the resonant frequency of the vibrations in said magnetostriction transducer.

6. A method as claimed in claim 3 wherein the analyzing of the frequency comprises detecting changes in the amplitude of the vibrations in said magnetostriction transducer at or around the resonant frequency.

7. A method as claimed in claim 3 wherein said varying magnetic field produces a magnetic flux and the analysing of the frequency comprises detecting changes in the magnetic flux.

8. A method as claimed in claim 1 wherein the vibrations are ultrasounds.

9. A method as claimed in claim 1 wherein the analyzing comprises displaying at least one from the group consisting of the pressure, force, temperature, density, vibration, viscosity and speed of sound in said fluid.

10. A method as claimed in claim 1 wherein the analyzing comprises producing a warning that at least one from the group consisting of the pressure, force, temperature, density, vibration, viscosity and speed of sound in said fluid is at a predetermined level.

11. A method of remotely detecting at least one from the group consisting of pressure, force, temperature, density, vibration, viscosity and speed of sound in a fluid in an article, the article having an inside and an outside, the method comprising:
   providing a magnetostriction transducer in the inside of the article,
   providing means to produce a varying magnetic field in spaced apart relationship with said magnetostriction transducer, positioning the means to produce a varying magnetic field outside the article, producing a varying magnetic field such that the varying magnetic field acts upon said magnetostriction transducer to generate vibrations in said magnetostriction transducer, providing means to detect the vibrations in spaced apart relationship with said magnetostriction transducer, positioning the means to detect the vibrations outside the article, detecting the vibrations generated in said magnetostriction transducer by the varying magnetic field, and analyzing the detected vibrations to determine at least one from the group consisting of the pressure, force, temperature, density, vibration, viscosity and speed of sound in a fluid, the article being a hollow article, said magnetostriction transducer comprising at least two magnetostriction transducers, a first one of the magnetostriction transducers being in communication with the hollow interior of the hollow article and the second one of the magnetostriction transducers being isolated from the hollow interior of the hollow article, said at least two magnetostriction transducers having different resonant frequencies.

12. An apparatus for remotely detecting at least one from the group consisting of pressure, force, temperature, density, vibration, viscosity and speed of sound in a fluid in an article, the article having an inside and an outside, the apparatus comprising a magnetostriction transducer positioned completely inside the article, means to produce a varying magnetic field arranged in spaced apart relationship with said magnetostriction transducer such that a varying magnetic field acts upon said magnetostriction transducer to generate vibrations in said magnetostriction transducer, the means to produce the varying magnetic field being positioned outside the article, means to detect the vibrations generated in said magnetostriction transducer, the means to detect the vibrations being arranged in spaced apart relationship with said magnetostriction transducer, the means to detect the vibrations being positioned outside the article, and analyzing means to analyze the detected vibrations to determine at least one from the group consisting of the pressure, force, temperature, density, vibration, viscosity and speed of sound in a fluid.

13. An apparatus as claimed in claim 12 wherein the article is a hollow article.

14. An apparatus as claimed in claim 12 wherein the means to analyze the detected vibrations comprises means to analyze the amplitude or the frequency or the damping or the phase.

15. An apparatus as claimed in claim 14 wherein means to analyze the damping comprises means to detect the decay rate of the amplitude of the vibrations in said magnetostriction transducer at a particular frequency.

16. An apparatus as claimed in claim 14 wherein the means to analyze the frequency comprises means to detect changes in the resonant frequency of the vibrations in said magnetostriction transducer.

17. An apparatus as claimed in claim 14 wherein the means analyze the frequency comprises means to detect changes in the amplitude of the vibrations in said magnetostriction transducer at or around the resonant frequency.

18. An apparatus as claimed in claim 12 wherein said magnetostriction transducer comprises a magnetostrictive member and a damping member secured to the magnetostrictive member, the damping member having a large surface area.

19. An apparatus as claimed in claim 12 wherein the magnetostrictive transducer comprises a magnetostrictive member and there are mechanical means to prestress the magnetostrictive member.

20. An apparatus as claimed in claim 19 wherein the magnetostriction transducer comprises magnetic means to magnetically bias the magnetostrictive member.

21. An apparatus as claimed in claim 19 wherein the magnetostrictive member comprises an alloy of terbium, dysprosium and iron.

22. An apparatus as claimed in claim 12 wherein the means to detect the vibrations comprises a coil of wire to detect changes in the generated magnetic field, which corresponds to the vibrations of said magnetostriction transducer.

23. An apparatus as claimed in claim 12 wherein the means to produce a varying magnetic field comprises a coil of wire.

24. An apparatus as claimed in claim 23 wherein the means to detect the vibrations comprises the coil of wire used to produce the varying magnetic field, the coil of wire detects changes in the generated magnetic field, which corresponds to the vibrations of the magnetostriction transducer.

25. An apparatus as claimed in claim 12 wherein the analyzing means has means to display the pressure, force, temperature, density, vibration, viscosity or speed of sound in said fluid.

26. An apparatus as claimed in claim 12 wherein the analyzing means has means to produce a warning that the pressure, force, temperature, density, vibration, viscosity or speed of sound in said fluid is at a predetermined level.

27. The apparatus as claimed in claim 12 wherein the article is a turbofan fan blade and the apparatus detects pressure or temperature.

28. An apparatus for remotely detecting at least one from the group consisting of pressure, force, temperature, density, vibration, viscosity and speed of sound in a fluid in an article, the article having an inside and an outside, the apparatus comprising a magnetostriction transducer positioned inside the article, means to produce a varying magnetic field arranged in spaced apart relationship with said magnetostriction transducer such that a varying magnetic field acts upon said magnetostriction transducer to generate vibrations in said magnetostriction transducer, the means to produce the varying magnetic field being positioned outside the article, means to detect the vibrations generated in said magnetostriction transducer, the means to detect the vibrations being arranged in spaced apart relationship with said magnetostriction transducer, the means to detect the vibrations being positioned outside the article, and analyzing means to analyze the detected vibrations to determine at least one from the group consisting of the pressure, force, temperature, density, vibration, viscosity and speed of sound in a fluid, said magnetostriction transducer comprising a magnetostrictive plate having a first face and a second face and a damping plate secured to the first face of the magnetostrictive plate.

29. An apparatus for remotely detecting at least one from the group consisting of pressure, force, temperature, density, vibration, viscosity and speed of sound in a fluid in an article, the article having an inside and an outside, the apparatus comprising a magnetostriction transducer positioned inside the article, means to produce a varying magnetic field arranged in spaced apart relationship with said magnetostriction transducer such that a varying magnetic field acts upon said magnetostriction transducer to generate vibrations in said magnetostriction transducer, the means to produce the varying magnetic field being positioned outside the article, means to detect the vibrations generated in said magnetostriction transducer, the means to detect the vibrations being arranged in spaced apart relationship with said magnetostriction transducer, the means to detect the vibrations being positioned outside the article, and analyzing means to analyze the detected vibrations to determine at least one from the group consisting of the pressure, force, temperature, density, vibration, viscosity and speed of sound in a fluid, wherein said magnetostriction transducer comprises a magnetostrictive member arranged in a sealed chamber, the sealed chamber being evacuated and defined by at least one flexible wall, the flexible wall being arranged permanently in contact with said magnetostrictive member.

30. An apparatus as claimed in claim 29 wherein the magnetostriction transducer comprises a rigid cylindrical wall having a rigid end wall and a flexible end wall defining the sealed chamber and a magnetostrictive member extending between and contacting the rigid end wall and the flexible end wall.

31. An apparatus as claimed in claim 30 wherein the rigid walls and the flexible wall comprise low magnetic permeability materials.

32. An apparatus as claimed in claim 30 or claim 31 wherein the rigid walls comprise stainless steel and the flexible wall comprises brass.

33. A magnetostriction transducer as claimed in claim 29 comprising a rigid cylindrical wall having a rigid end wall and a flexible end wall defining the sealed chamber and a magnetostrictive member extending between and contacting the rigid end wall and the flexible end wall.

34. An apparatus for remotely detecting at least one from the group consisting of pressure, force, temperature, density, vibration, viscosity and speed of sound in a fluid in an article, the article having an inside and an outside, the apparatus comprising a magnetostriction transducer positioned inside the article, means to produce a varying magnetic field arranged in spaced apart relationship with said magnetostriction transducer such that a varying magnetic field acts upon said magnetostriction transducer to generate vibrations in said magnetostriction transducer, the means to produce the varying magnetic field being positioned outside the article, means to detect the vibrations generated in said magnetostriction transducer, the means to detect the vibrations being arranged in spaced apart relationship with said magnetostriction transducer, the means to detect the vibrations being positioned outside the article, and analyzing means to analyze the detected vibrations to determine at least one from the group consisting of the pressure, force, temperature, density, vibration, viscosity and speed of sound in a fluid, wherein said magnetostriction transducer comprises a magnetostrictive member arranged in a sealed chamber, the sealed chamber being evacuated and defined by at least one flexible wall, the flexible wall being arranged to move into and out of contact with said magnetostrictive member.

35. An apparatus as claimed in claim 34 wherein said magnetostriction transducer comprises a rigid cylindrical wall having a rigid end wall and a flexible end wall defining the sealed chamber and a magnetostrictive member extending between and contacting the rigid end wall and the flexible end wall.

36. An apparatus for remotely detecting at least one from the group consisting of pressure, force, temperature, density, vibration, viscosity and speed of sound in a fluid in an article, the article having an inside and an outside, the apparatus comprising a magnetostriction transducer positioned inside the article, means to produce a varying magnetic field arranged in spaced apart relationship with said magnetostriction transducer such that a varying magnetic field acts upon said magnetostriction transducer to generate vibrations in said magnetostriction transducer, the means to produce the varying magnetic field being positioned outside the article, means to detect the vibrations generated in said magnetostriction transducer, the means to detect the vibrations being arranged in spaced apart relationship with said magnetostriction transducer, the means to detect the vibrations being positioned outside the article, and analyzing means to analyze the detected vibrations to determine at least one from the group consisting of the pressure, force, temperature, density, vibration, viscosity and speed of sound in a fluid, wherein said magnetostriction transducer comprises at least two magnetostriction transducers, a first one of the magnetostriction transducers being in communication with the hollow interior of the hollow article and the second one of the magnetostriction transducers being isolated from the hollow interior of the hollow article, said at least two magnetostriction transducers having different resonant frequencies.

37. An apparatus for remotely detecting at least one from the group consisting of pressure, force, temperature, density, vibration, viscosity and speed of sound in a fluid in an article, the article having an inside and an outside, the apparatus comprising at least one magnetostriction transducer positioned inside the article, means to produce a varying magnetic field arranged in spaced apart relationship with the magnetostriction transducer such that a varying magnetic field acts upon the at least one magnetostriction transducer to generate vibrations in the at least one magnetostriction transducer, the means to produce the varying magnetic field being positioned outside the article, means to detect the vibrations generated in the at least one magnetostriction transducer, the means to detect the vibrations being arranged in spaced apart relationship with the magnetostriction transducer, the means to detect the vibrations being positioned outside the article, and analyzing means to analyze the detected vibrations to determine at least one from the group consisting of the pressure, force, temperature, density, vibration, viscosity and speed of sound in a fluid, wherein the at least one magnetostriction transducer comprises a magnetostrictive member arranged in a sealed chamber, the sealed chamber being evacuated.

* * * * *